United States Patent
White

(10) Patent No.: US 8,021,405 B2
(45) Date of Patent: Sep. 20, 2011

(54) TREATMENT OF EAR INFECTION USING BLUE/VIOLET LIGHT

(76) Inventor: Susan Lemons White, Raleigh, NC (US)

( * ) Notice: Subject to any disclaimer, the term of this patent is extended or adjusted under 35 U.S.C. 154(b) by 0 days.

(21) Appl. No.: 11/952,067

(22) Filed: Dec. 6, 2007

(65) Prior Publication Data

US 2009/0149922 A1    Jun. 11, 2009

(51) Int. Cl.
*A61N 5/06* (2006.01)
(52) U.S. Cl. .............................. 607/88; 606/9; 128/898
(58) Field of Classification Search ................ 606/2–19; 607/88–94; 128/898
See application file for complete search history.

(56) References Cited

U.S. PATENT DOCUMENTS

| | | | |
|---|---|---|---|
| 4,658,823 A | 4/1987 | Beddoe et al. | |
| 4,865,035 A | 9/1989 | Mori | |
| 5,292,346 A | 3/1994 | Ceravolo | |
| 6,389,313 B1 * | 5/2002 | Marchitto et al. | 604/21 |
| 6,443,978 B1 * | 9/2002 | Zharov | 607/91 |
| 6,524,329 B1 | 2/2003 | Benedict | |
| 6,596,016 B1 | 7/2003 | Vreman et al. | |
| 6,953,341 B2 | 10/2005 | Black | |
| 7,020,902 B1 * | 4/2006 | Tyler | 2/209 |
| 7,377,666 B1 * | 5/2008 | Tyler | 362/105 |
| 2003/0009158 A1 | 1/2003 | Perricone | |
| 2004/0122492 A1 | 6/2004 | Harth et al. | |
| 2004/0176823 A1 | 9/2004 | Island et al. | |
| 2005/0137656 A1 * | 6/2005 | Malak | 607/88 |
| 2005/0149149 A1 | 7/2005 | Chung et al. | |
| 2006/0271024 A1 * | 11/2006 | Gertner et al. | 606/2 |
| 2008/0046042 A1 * | 2/2008 | Branch | 607/88 |
| 2008/0119914 A1 * | 5/2008 | Rose et al. | 607/88 |

FOREIGN PATENT DOCUMENTS

EP    1889637 A1 *    2/2008

OTHER PUBLICATIONS

Definition of Chronic Otitis externa, http://www.medterms.com/script/main/art.asp?articlekey=21339.
Middle ear, http://en.wikipedia.org/wiki/Middle_ear.
Otitis media, http://en.wikipedia.org/wiki/Otitis_media.
Otitis externa, http://en.wikipedia.org/wiki/Otitis_externa.

* cited by examiner

*Primary Examiner* — Henry M Johnson, III
*Assistant Examiner* — Lynsey Crandall
(74) *Attorney, Agent, or Firm* — Jim Passé; Passé Intellectual Property, LLC

(57) ABSTRACT

The present invention relates to the treatment of Otitis or other type ear infections with the use of blue/violet light positioned to shine into the ear canal. The treatment quickly clears up infections and reduces the reoccurrence of ear infections.

5 Claims, No Drawings

TREATMENT OF EAR INFECTION USING BLUE/VIOLET LIGHT

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to the treatment of ear infections. More specifically the present invention relates to the treatment of ear infections with blue/violet light therapy.

2. Description of Related Art

Otitis media is an inflammation of the middle ear: the space behind the ear drum. It is one of the two conditions that are commonly thought of as ear infections, the other being Otitis externa. Ear infections are very common in childhood, and includes acute and chronic conditions; all of which involve inflammation of the ear drum (tympanic membrane), and are usually associated with a buildup of fluid in the space behind the ear drum (middle ear space).

Inflammation of the skin of the ear canal is the essence of this disorder. If inflammation progresses to infection, the ear canal may fill with swollen tissue and drainage. Once the ear canal is blocked, hearing will be dampened (conductive hearing impairment) until the condition improves. In very severe cases, the skin infection can spread to the face (facial cellulitis) and to the major salivary gland in the cheek (parotitis). In that situation, moving the jaw and eating become painful. In its mildest forms, external Otitis is so common that some ear nose and throat physicians have suggested that most people will have an episode at some point in life. In many individuals, for the reasons discussed below, the condition is chronic, especially when the ear canal gets damp, and infections occur repeatedly during the patient's lifetime (chronic Otitis).

The use of topical solutions and suspensions in the form of ear drops and ear spray are the current mainstay of treatment for external Otitis. These drops both physically wash collected debris, shed skin and infected drainage from the ear canal, and contain substances that either kill pathogenic germs, stop them from multiplying, or do both. The drops generally contain drying substances (astringents), acidifying agents, antibiotics and/or antifungal agents. Some prescription drops also contain anti-inflammatory steroids. Although there is evidence that steroids are effective at reducing the length of treatment time required, fungal Otitis may be aggravated by the use of topical steroids.

When the condition has progressed to the point where the ear canal is blocked, a physician may have to begin treatment by clearing the ear under otoscopic examination and placing a thin strip of an absorbent material (ear wick) into the ear canal. In severe cases of external Otitis, an otologist is needed to carefully clean out the ear canal under microscopic visualization. In such severe cases, in which drainage is abundant enough to recurrently block the ear canal, a qualified health professional may aspirate the ear as many times as twice a week for the first two or three weeks of treatment. It is imperative that there is visualization of an intact tympanic membrane. Use of certain medications with a ruptured tympanic membrane can cause tinnitus, vertigo, dizziness and hearing loss in some cases.

Although the acute infection of external Otitis generally resolves in a few days with topical washes and antibiotics, it normally takes weeks before the ear canal skin is fully normal. The glands of the outer skin of the ear canal will not begin producing cerumen again until the skin is not only no longer infected, but no longer inflamed. Once healed completely, the ear canal is again self-cleaning. Until then, slight irritation or dampness can be enough to cause external Otitis to flare again.

As stated above effective medications include ear drops or sprays containing antibiotics to fight infection, and corticosteroids to reduce itching and inflammation. The first line is currently a topical preparation such as 2% acetic acid or a topical antibiotic solution containing antibiotics such as aminoglycoside, polymyxin or fluoroquinolone. It is possible to have both a bacterial and fungal ear infection, and many of the topical treatments are designed to cure both.

Occasionally, pills may be used in addition to the topical medications. Analgesics may be used if pain is severe. Putting something warm against the ears may reduce pain.

Light of various frequencies has been used to treat various conditions including acne and various bacterial infections on the face and throat. In US published patent application 2003/0009158 discloses skin treatments using blue and violet light. Aging or damaged skin is treated by irradiating affected skin areas with an effective amount of light. The light can be from a light source or from sunlight. In addition, treatment of the skin with light and compositions which enhance light penetration are disclosed.

In U.S. Pat. No. 6,953,341 to Black issued Oct. 11, 2005 there is disclosed a "toothpick" for the light treatment of body structures. The device has a handle and a tapered element for delivering light of various frequencies. As the name "toothpick" implies, the device is designed essentially for use as an oral hygiene device. While a number of uses are listed there are no examples of the device using any particular light frequency or that any particular disease is treatable with the device. In addition, the device comprises a massaging means for massaging the gums or other oral structures. The large size and tapered nature of the device as well as the vibratory nature of the device make it unsuitable sensitive structures such as the ear and useful only for oral or like structures. Further, the device provides not only blue and violet light it provides green light as well as a means for using the device to massage the body structure the device is used on.

In U.S. Pat. No. 5,292,346 to Ceravolo issued Mar. 8, 1994 there is described a bactericidal ultraviolet light radiating device for the treatment of mucosal or dermal tissues having a light source, optical light directing lens coupled to the light source and an electric power supply to power the light source. The device is described as intended for oral therapeutic radiation application of ultraviolet light (below about 400 nanometers in wavelength). While it is described as being able to be used in the ear no discussion of the effectiveness of the design or of actual use in the ear is described.

In U.S. Pat. No. 4,865,035 to Mori, there is described a device which delivers the entire visible spectrum of light designed to be close to the entire suns visible spectrum. The invention is described as safer than use of ultraviolet light however requires use of a long probe light source which could be detrimental if inserted in the ear but necessary to deliver natural light of this particular invention. No indication that broad spectrum light does anything to treat ear infections and in fact broad spectrum light natural light does not appear to work as a cure for Otitis.

Use of blue/violet light has been well documented as useful in the treatment of skin conditions such as acne vulgaris. It has been demonstrated that the main bacteria involved in acne the P acnes bacteria which is the cause of the acne skin lesions is sensitive to this light range. For example in US patent publication 2004/0122492 to Harth, et al, there is described a large device for combining both blue/violet and IR light to treat skin conditions and in US patent publication 2004/0176823 to Island et al there is described a novel device for the treatment of acne using a blue/violet diode light source.

Accordingly there is a need in the art for new and useful treatments for ear infections other than the presently known treatments.

SUMMARY OF THE INVENTION

It has been surprisingly discovered that a treatment of an infection of the ear canal, even in individuals who suffer from chronic or persistent ear infections, can effectively be treated with an exposure of a concentrated source of light consisting of blue/violet light into the ear canal.

Accordingly, in one embodiment of the invention there is disclosed a method of treating an ear infection comprising administering an effective amount of light consisting of a frequency from about 400 nanometers to about 500 nanometers sufficient to reduce or eliminate the organism causing the infection.

In another embodiment of the invention there is disclosed a method of treating a human having an infection in the ear canal comprising positioning a device consisting of an LED light consisting of a frequency from about 400 nanometers to about 500 nanometers at the opening of the ear canal an infected ear, emitting light from the device into the ear canal, exposing the canal to sufficient light to reduce or eliminate the infection.

These and other objects of the present invention will be clear when taken in view of the detailed specification and disclosure in conjunction with the appended figures.

DETAILED DESCRIPTION OF THE INVENTION

The general description of the invention and how to use the method of treatment is stated in the Brief Summary above. This detailed description defines the meaning of the terms used herein and specifically describes embodiments in order for those skilled in the art to practice the invention. The above interests in successfully treating ear infections can be seen from the disclosure which follows and are met by the present invention.

As used herein "ear infection" relates to an infection of some portion of the ear canal of a human. This, in general, will be any portion of the ear canal that the light of the present invention can penetrate to, that has been infected by an organism. The organism would, in general, be an organism that is typical of the Otitis type infections of the ear. Since the light of the invention is positioned at the opening to the ear canal, light from a device will penetrate the exterior ear canal most effectively followed by the middle and inner ear canal. Adjustments in intensity of the light source for the present invention can be made to most effectively treat the infection based on the position of the infection within the ear canal.

As used herein the phrase "administering an effective amount" means to expose the light of the present invention to the ear canal for sufficient length time, sufficient number of times and in amounts and energy levels sufficient to provide an observable improvement in the ear infection either by a reduction, elimination or a decrease in the time of the infection. One skilled in the art in view of this disclosure could, without undue experimentation select light sources of different wattages, intensities and the like consistent with the disclosure herein. In another embodiment both ears are treated with separate light sources simultaneously.

"Sufficient" amounts of light and energy can be accomplished by a single exposure of a given time or multiple exposures of fixed or varying length of time depending on the position of the infection in the canal, as well as the intensity of the infection. In one embodiment a single exposure is from about 6 to 10 minutes could be sufficient to treat or prevent the progression of an ear infection. Chronic or more intense infections would require a more intense treatment for example in one embodiment the treatment would be for 15 minutes from about 2 to 5 times daily. In another embodiment, one skilled in the art could easily, with the information herein, decide the length of treatment, the frequency as well as the amount of light to treat a particular case without undue experimentation.

As used herein "light" refers to an artificial source of light of the frequency of the present invention namely, consisting of about 400 to about 500 nanometers. The frequency of a given light source of the present invention can be across the entire range, a portion of the range or can be limited to a single frequency within the range. Since the light is positioned very close to a sensitive body structure, the ear, the light source should be one that does not generate large amounts of heat when in use nor should the light source bulb be excessively large. The source of the light in one embodiment is a "blue LED". The blue LED is known to be within the range necessary for treatment in the present invention, does not generate large amounts of heat, is relatively small and can deliver light to the ear canal without fear of the damaging effects of a larger bulb or many other light sources. In addition, LED bulbs can be made into hands free battery operated units. In one embodiment the LED light bulbs have a light output of about 0.7 lumens at about between 3.2 and 3.6 volts.

As used herein "reduce or eliminate the infection" refers to the action of the light in the range of the present invention to significantly increase the death rate or completely kill the organism(s) responsible for the ear canal infection.

By "hands free" as used herein, refers to a battery operated light source, such as a battery operated LED, which is designed to hang on the ear with the light source positioned at the opening of the ear canal. The light would provide an effect without having to hold the device, move it about or be connected to a power source. This could be accomplished, in one embodiment, with a battery operated LED device designed to be positioned with the LED facing the ear canal opening. In another embodiment the device covers the entire ear canal so that light does not leak out of the ear canal and a maximum amount of energy is directed or reflected off the device into the ear canal. One such unit is described in a co-filed application to the present inventor having application Ser. No. 11/952,061, which is incorporated herein by reference in its entirety.

In use the present invention method would be accomplished as follows. After determining that the ear of a particular human patient is infected, such as by visual observation, description of symptoms or by known culturing methods the present invention would be commenced. A device with a blue/violet light source (and no other light frequencies), would be selected and positioned at the opening of the ear canal. The light source would be positioned such that it faced directly into the ear canal. The device would then be turned on and the ear canal bathed in blue/violet light for the period of time selected based on the location and intensity of infection.

The light would remain on for a selected period of time and the treatment could be repeated either for a fixed number of treatments or repeated treatments could be accomplished and repeated until the infection is partially or completely cured. The cure would be evidenced by a reduction or elimination of symptoms including inflammation, ear pain and itching. In one embodiment the present treatment of the invention is further combined with known pharmaceutical treatments such as drops, antibiotics or the like to act faster and more thoroughly than a pharmaceutical treatment which is currently the only method of treating ear infections. In some embodiments the light treatment alone is sufficient.

When selecting the light source one embodiment uses a device which attaches to the ear, head or the like and is self supporting in its position the light facing the infected ear canal. A battery operated embodiment means that the device can be worn while doing other tasks and one would not have to sit with the limitations of cord length nor the dangers of an AC current device close to a sensitive body structure.

EXAMPLE 1

A 55 year old female suffering from chronic ear infections was determined to have an ear canal infection. A flashlight type LED device having a blue LED and having a light output of from about 465 nm to 475 nm and a luminosity intensity MCD of between about 11,000 and 13,000 with a DC Forward voltage of between about 3.2 and 3.6 Volts, was positioned at the opening of the ear canal and the light turned on. Light treatment consisted of treatment to the ear canal for a period of 15 minutes twice a day for three days. At the end of the first three days the patient reported considerable relief from ear pain and itching. Treatment was continued for 15 minutes once a day for three days until the infection was cleared.

EXAMPLE 2

The patient was treated once for 15 minutes any time the ear canal got wet. Patient reported a reduction in the number and intensity of infections. After such routine treatment subsequent infections that did occur could pain and itching could be relieved with one therapy of between 5 to 8 minutes.

While the particular patient had infections that lasted several days, after treatment with the method of the invention using a blue LED the infection was completely eradicated within 48 hours after the first treatment.

The above description and example are for the purpose of teaching the person of ordinary skill in the art how to practice the present invention and it is not intended to detail all those obvious modifications and variations of it which become apparent to the skilled worker upon reading the present invention description. It is intended, however, that all such modifications and variations be included within the scope of the present invention, which is defined by the following claims. The claims are intended to cover the claimed steps and components, in any sequence, consistent with the present invention which is effective to meet the objectives herein intended unless the context specifically indicates to the contrary.

What is claimed is:

1. A method of treating or preventing external Otitis or chronic external Otitis infection comprising:
    a) selecting an individual that has been determined to be infected with external Otitis or is subject to chronic external Otitis;
    b) selecting an LED consisting of a wavelength of from about 400 to about 500 nanometers, and having a light output of 0.7 lumens;
    c) positioning the LED at the opening of the ear canal in a manner such that the device is not inserted in the ear canal of the individual, facing the ear canal opening; and
    d) exposing the ear canal to the light from the LED for 6 to 75 minutes per day sufficient to treat or prevent the infection.

2. The method according to claim 1 comprising the step of exposing the ear canal to the LED multiple times per day.

3. The method according to claim 1 for treating or preventing chronic external Otitis comprising the step of exposing the ear canal to the LED for 15 minutes from 2 to 5 times daily.

4. The method according to claim 1 wherein a single exposure is from 6 to 15 minutes.

5. The method according to claim 4 wherein the single exposure is from 6 to 10 minutes.

* * * * *